United States Patent [19]

Kenney

[11] 4,029,530

[45] June 14, 1977

[54] METHOD OF FORMING LEAD STYPHNATE AMMUNITION PRIMING MIXTURE

[75] Inventor: Joseph F. Kenney, Bridgeport, Conn.

[73] Assignee: Remington Arms Company, Inc., Bridgeport, Conn.

[22] Filed: Feb. 12, 1976

[21] Appl. No.: 657,487

Related U.S. Application Data

[63] Continuation-in-part of Ser. No. 489,704, July 18, 1974, abandoned.

[52] U.S. Cl. .................................. 149/28; 149/27; 149/24

[51] Int. Cl.² .......................................... C06B 41/06

[58] Field of Search ........................ 149/24, 27, 28; 260/435 A

[56] References Cited

UNITED STATES PATENTS

| | | | |
|---|---|---|---|
| 1,443,328 | 1/1923 | Herz | 149/24 |
| 1,999,728 | 4/1935 | Herz | 149/24 |
| 2,150,653 | 3/1939 | Franz | 260/435 A |
| 2,239,547 | 4/1941 | Brun | 149/24 |
| 2,295,104 | 9/1942 | Garfield | 149/24 |
| 2,589,703 | 3/1952 | Kenney | 149/24 |
| 2,702,745 | 2/1955 | Kenney | 149/24 |
| 3,002,012 | 9/1961 | Backensto | 260/435 A |
| 3,301,882 | 1/1967 | Taylor | 260/435 A |
| 3,320,104 | 5/1967 | Stadler | 149/24 |

*Primary Examiner*—Edward A. Miller
*Attorney, Agent, or Firm*—John H. Lewis, Jr.; Nicholas Skovran; William L. Ericson

[57] ABSTRACT

Ammunition rim fire priming mixtures are commonly prepared by mixing normal lead styphnate, a sensitizer, such as tetracene, an oxygen donor such as lead nitrate, and a frictionator such as ground glass. This invention relates to such a mixture and to center fire priming mixtures which consist of lead styphnate, tetracene, inorganic fuels and barium nitrate and to a method of forming them and is characterized by the use of lead styphnate which is formed in situ by the reaction of a water wet mixture of styphnic acid and a lead compound such as lead oxide (litharge), lead hydroxide, basic lead carbonate, or lead carbonate. Important advantages of this invention are reduced cost, improved safety since it is unnecessary to prepare, precipitate, or separately handle pure or relatively pure lead styphnate and improved percussion sensitivity of the resulting mixtures.

5 Claims, No Drawings

METHOD OF FORMING LEAD STYPHNATE AMMUNITION PRIMING MIXTURE

This application is a continuation-in-part of my application Ser. No. 489,704, filed July 18, 1974, and now abandoned.

BACKGROUND OF THE INVENTION

Normal lead styphnate (normal lead trinitroresorcinate) is a well-known primary explosive which has been widely used for the manufacture of percussion primers for small arms ammunition and the like where it first came into use as a replacement for fulminate of mercury. Normal lead styphnate is a very powerful, percussion sensitive explosive which is also quite sensitive to static electricity. The danger of handling it in pure, or relatively pure form, is such that it is normally handled only in small quantities, kept wet, and in rubber containers or "boats." Even with these precautions it has been known to detonate as the result of the stimuli of shock, friction, static electricity, or exposure to sparks or flame.

The normal lead styphnate of this invention is prepared in situ in a wet mixture of styphnic acid (trinitroresorcine) and a lead compound such as lead oxide (litharge), lead hydroxide, basic lead carbonate, or lead carbonate. In the resulting wet mixture the lead styphnate does not show any undesirable sensitivity to initiation by shock, friction, or static electricity and such wet mixtures can be handled in normal primer charging operations with little or no risk of accidental explosion.

As set forth in Davis "The Chemistry of Powder and Explosives," Page 440, Vol. II (1943) John Wiley and Sons Inc.,lead styphnate is commonly prepared by adding a solution of magnesium styphnate at 70° C. to a well stirred solution of lead acetate at 70° C. A voluminous precipitate of the basic salt separates. The mixture is stirred for 10 or 15 minutes; then dilute nitric acid is added with stirring to convert the basic salt to the normal salt and the stirring is continued while the temperature drops to about 30° C. The product, which consists of reddish-brown, short, rhombic crystals, is filtered off, washed with water, sieved through silk, and dried. In the processes of filtration and washing undesirable impurities tend to be eliminated.

Other methods of producing normal lead styphnate are described in the patents of Edmund Herz, such as No. 1,443,328 and No. 1,999,728, the latter process having been used commercially for many years in the making of many millions of small arms primers. This latter method is characterized by the preparation of lead styphnate by the interaction of a concentrated solution of magnesium styphnate with a solution of lead nitrate in the presence of free styphnic acid.

The patent to Brun No. 2,239,547 proposes to make a priming mixture by mixing moist mono-basic lead styphnate with moist styphnic acid and other priming mixture ingredients such as a sensitizer, an oxidizer, and an abrasive. However, mono-basic lead styphnate is itself a dangerously sensitive primary explosive and by practicing the Brun invention it would not be possible to achieve the chief advantages of applicant's method as later hereinafter set forth.

When the first attempts were made to produce lead styphnate in accordance with the present invention, commercial styphnic acid was used and the resulting mixtures were found to be so sticky that they clung to the charging equipment and were found to harden to an undesirable degree preventing charging when the wet mixtures were stored for such periods as overnight.

In the commercial manufacture of styphnic acid, resorcinol is first sulphonated with 90% sulphuric acid. After the sulphonation is complete, nitric acid is added, the material nitrated and the styphnic acid precipitated. Some investigators (Franz, Wilkinson and Ehrlich U.S. Pat. No. 2,150,653) feel that when styphnic acid is so manufactured on a commerical scale, small amounts of nitrous and nitric oxides are present during the sulphonation. This, they felt, produces a dark brown material which may include some or all of the nitro derivatives of resorufin, the nitro derivatives of indo-phenol and the nitro derivatives of resazurin.

I have also discovered that styphnic acid produced by one of the commercial processes contains a minor amount of sulphuric acid. When styphnic acid is dissolved in amyl alcohol and the amyl alcohol solution extracted with water several times, the water extracts may be bulked together, evaporated to one-half volume, chilled, and the precipitated crystals of styphnic acid removed by filtration. Successive repetitions of this technique of evaporating the water extract, cooling it to precipitate any remaining styphnic acid, filtering out the crystals, etc. followed by evaporation as far as possible in a steam bath and by evaporation in a vacuum oven at 65° C resulted in the concentration of a black oily residue. This oily residue was found to have as its principal ingredient sulphuric acid which was undoubtedly carried over from the sulphonation process. Other impurities are also present in the oily residue and are believed to consist of one or more of the impurities referred to in the aforementioned Patent No. 2,150,653 or in a later patent to one of the same inventors, Patent No. 2,246,963.

As will be noted from these patents, it was theorized that the presence of these impurities was helpful in the manufacture of lead styphnate and if the styphnic acid was too pure it was the practice of these inventors to add one or more of such impurities or to modify the process to insure that they would be produced.

Certainly the presence of these impurities had no adverse effects in the formation of lead styphnate by the methods of the prior art for in the precipitation, filtering, washing and drying of the lead styphnate, the impurities or lead salts formed from reactions with such impurities, were readily separated from the dense crystalline normal lead styphnate.

However, in the practice of applicant's process, wherein the normal lead styphanate is precipitated in situ in a priming mixture, there is no opportunity to eliminate the impurities or any products resulting from a reaction with the impurities. Although the impurities do not interfere with the production of the lead styphnate, by remaining in the mixture they profoundly affect the resulting mixture and it may become so sticky that it adheres to tools and charging plates and hence cannot be charged into primers in the usual way and the mixtures may harden up so quickly that they cannot be stored for the required length of time or handled in the normal manner.

Accordingly, when referring to lead styphnate for use in my invention, I refer to relatively pure styphnic acid in the form of dense crystals of reasonably uniform shape and size and of the light color associated with the pure product. The dark brownish commercial styphnic acid or any other form of styphnic acid containing significant amounts of impurities such as sulphuric acid, the nitro derivatives of resorufin, the nitro derivatives of indophenol and the nitro derivatives of resazurin should not be used.

As has been indicated, there are known prior art methods of producing styphnic acid of the desired purity and the usual commercial styphnic acid may be adequately purified by dissolution and re-crystallization. It has also been noted that with some of the forms of commercial styphnic acid the dry product may be selectively screened to eliminate irregular, large, agglomerated forms. It may be that these irregular, large, agglomerated forms are constituted of a mass of fine particles bound together on a globule of sulfuric acid carried over from the sulphonation process.

SUMMARY OF THE INVENTION

The present invention resides primarily in the discovery that water wet relatively pure styphnic acid may be reacted directly with an inorganic non-explosive lead compound such as lead oxide, lead hydroxide, basic lead carbonate, or lead carbonate to form lead styphnate in situ in the wet mixture and that this wet product may be combined directly with the other normal ingredients of a priming mixture which may then be wet charged into primer cups without ever separating out or handling the lead styphnate in any dangerous or electrostatically sensitive conditions.

The chief advantage of this in situ method of manufacturing priming mixtures are:

1 Substantial cost reduction through the elimination of the separate manufacture of lead styphnate;

2 Greatly increased safety through the elimination of the necessity to handle pure lead styphnate as a separate ingredient;

3 Reduction of environmental pollution potential through the elimination of certain production wastes which were inherent in the prior art processes for the production of lead styphnate;

4 Improved percussion sensitivity of the resulting mixtures;

5 The only by-products of the reaction are water or water and carbon dioxide, thus nothing is left which contaminates the mixture.

DESCRIPTION OF THE PREFERRED PROCESSES

As indicated, the key feature of this invention is the direct reaction between water wet relatively pure styphnic acid crystals and an inorganic non-explosive lead compound such as lead oxide or lead hydroxide. As indicated, it is desirable that the styphnic acid be a relatively pure form and at least free from such impurities as sulphuric acid, the nitro derivatives of resorufin, the nitro derivatives of indophenol and/or the nitro derivatives of resazurin. If styphnic acid used in the preferred process contains such impurities, there is no opportunity to eliminate any undesirable products of a reaction with the impurity so that the undesirable products remain in the lead styphnate produced in situ and cause stickiness and premature hardening of the mixture. Water or water and carbon dioxide are readily eliminated in further processing and there are no other by-products of the reaction.

Although it is desirable that the reaction product be incorporated directly into a conventional priming mixture it is important that, at the time the reaction referred to above takes place, certain of the other usual ingredients of a priming mixture should not be present in the reacting mass unless it can be established that such ingredients do not themselves react with one or the other of the reactants or with any intermediate compounds which may be formed. Thus, it has been established that gum arabic in water solution which is usually employed as a binder in wet priming mixtures, may be present while the reaction is going on, does not enter into that reaction, and may be desirable through its contribution to the mixability of the mixture and its effect in minimizing any tendency of the mixture to dry prematurely. Similarly, tetracene (1-Guanyl-4-nitrosoaminoguanyltetrazene) a commonly used sensitizer in ammunition priming mixtures, may be present during the reaction, does not enter into that reaction and is helpful in that the water content which is essential for the safe handling of tetracene contributes to maintaining the necessary moist environment for the reaction to proceed.

The other usual constituents of a priming mixture such as oxygen donors, fuels, an frictionators are preferably incorporated into the wet mixture after the lead styphnate reaction has been completed and prior to charging the wet mixture into rim fire cartridges or primer cups. As is the usual practice with wet charged mixtures, drying takes place after charging has been completed and the explosives do not return to their normal sensitivity until after drying. Thus, at no stage in the processing is there any occasion to handle dangerously sensitive explosives in bulk or to manipulate them when they are in a dry or otherwise dangerously sensitive condition.

A preferred method of preparing a rim fire priming composition in which the principal explosive ingredient is lead styphnate is as follows:

EXAMPLE I 3 lbs., 13 oz. (1,729 grams) of styphnic acid (wet weight with 20% water) is added to 3 oz. (85 grams) of gum arabic solution of a concentration of 4 lbs., 6 oz. (1,871 grams) gum arabic in 8 lbs., 13 oz. (4,000 grams) water and 12 oz. (340 grams) of tetracene (wet weight with 33% water) in the kettle of an industrial type Hobart mixer.

These ingredients are premixed for 1 minute in the Hobart mixer at room temperaure of about 72° F.

To this premix there is added 1 lb., 12 oz. (794 grams) of lead hydroxide (wet weight with 15% water) and these ingredients are mixed in the Hobart mixer for about 4 minutes. As the ingredients react the temperature may rise to about 102° F.

An additional quantity of 1 lb., 12 oz. (794 grams) of lead hydroxide (wet weight with 15% water) is added and mixing continued in the Hobart mixer for an additional 4 minute period during which the temperature may rise to about 116° F. At this point, the reaction producing lead styphnate has been completed and the explosive ingredients of lead styphnate and tetacene are intimately mixed in a moist plastic mass with the gum arabic binder. Completion of the reaction may be verified by inspection of a sample at this point. This mixture does not require washing, filtering, or drying and except for the excess water which keeps it wet and insensitive, there is no waste product to be disposed of. It is preferable that the lead hydroxide be added in two steps as above, both by reason of the completeness of the reaction and the type of lead styphnate resulting as will be more fully discussed below.

As an aid to visual inspection of primed rim fire shells, it is now preferable to add about one scoop (½ oz. or 14 grams) of an inert dye such as Prussian blue which is thoroughly blended by mixing for 4 minutes in the Hobart mixer. The resulting green-colored mixture contrasts sharply with the brass interior of a rim fire case and is much more apparent on visual inspection than the yellowish color characteristic of the lead styphnate and tetracene mistures. During this mixture cycle the mixture can be expected to cool to about 106° F.

At this point, the remaining ingredients of a rim fire priming mixture may be formed into a premix of the oxygen donor, barium nitrate, and the frictionator, ground glass. 2 lbs., 2 oz. (963 grams) of barium nitrate (dry weight) and 4 lbs., 2 oz. (1,869 grams) of ground glass (dry weight) are separately premixed and then blended with the explosive ingredients during two successive 2 minute mixing cycles in the Hobart mixer.

The yield is about 14½ lbs. (6,590 grams) of moist plastic rim fire priming mixture which is insensitive to shock, friction, and static electricity and which cannot even be detonated by the explosion of a blasting cap buried in the plastic mixture. As a result the mixture can be safely handled and can be extruded through metering devices or rubbed into the measuring apertures of the conventional charging plates without fear of accidental explosion.

Obviously, the mixture should be kept wet and plastic until used and the usual precautions should be observed to avoid the possibility that any of the mixture dries on or in charging equipment, storage receptacles and the like. Any mixture which is allowed to become dry or which hardens to such a degree as to become unworkable should be handled and disposed of with all of the precautions appropriate to sensitive primary explosives. The mixture is dried after charging into rim fire shells and thereafter exhibits normal percussion sensitivity and igniting power.

A similar procedure using lead oxide (litharge) as one of the reactants is set forth below in the production of an equivalent rim fire priming mixture.

EXAMPLE II 3 lbs., 13 oz. (1,729 grams) of styphnic acid (wet weight with 20% water) is added to 7 oz. (198 grams) of water and 3 oz. (85 grams) of gum arabic solution, of a concentration of 4 lbs., 6 oz. (1,871 grams) gum arabic in 8 lbs., 13 oz. (4,000 grams) of water and 12 oz. (340 grams) of tetracene (wet weight with 33⅓% water) and two scoops of Prussian blue dye in the kettle of an industrial type Hobart mixer. These ingredients are premixed for 1 minute in the Hobart mixer at room temperature of about 72° F.

A hollow is formed in the center of the mass of moist premix by working with the hands or with a rubber spatula and in this hollow there is added 1 lb., 7 oz. (652 grams) of litharge, PbO (dry weight) and these ingredients are mixed in the Hobart mixer for about 3 minutes. As the ingredients react, the temperature may rise to about 114° F.

Another hollow is formed in the center of the mass of the partially reacted mix and an additional quantity of 1 lb., 7 oz. (652 grams) of litharge (dry weigth) is added in this hollow and mixing continued in the Hobart mixer for a period of about 4 minutes during which the temperature may rise to about 124° F. Mixing may be continued for an additional period of 4 minutes during which the temperature may be expected to drop to about 106° F.

At this point, the remaining ingredients of a rim fire priming mixture may be added such as the oxygen donor, barium nitrate and a frictionator, ground glass. 2 lbs., 2 oz. (963 grams) dry weight of barium nitrate and 4 lbs., 2 oz. (1,869 grams) dry weight of ground glass are separately premixed and then blended with the moist explosive ingredients produced above during two successive 2 minute mixing cycles with the Hobart mixer.

The yield is about 14⅓ lbs. (6,500 grams) of moist, plastic, rim fire priming mixture which is in all respects equivalent to that produced in EXAMPLE I and which is charged, dried, and used in the same way.

EXAMPLE III

A shotshell priming mixture may be produced by the following procedure:

278 grams of styphnic acid (wet with 20% water) are added to 10 cc's of gum arabic solution (2,090 grams gum arabic in 4,000 cc's water) and 60 grams of tetracene (wet, with 33% water) in the kettle of an industrial type Hobart mixer.

These ingredients are premixed in the Hobart mixer for 1 minute at room temperature which in this instance was 79° F.

To this premix there is added 129 grams of lead hydroxide (wet with 15% water) and these ingredients are mixed in the Hobart mixer for about 4 minutes. As the ingredients react the temperature may rise to about 95° F.

An additional quantity of 129 grams of lead hydroxide (wet with 15% water) is added and mixing continued for about another 4 minutes during which the temperature may rise to about 108° F.

To form a typical shotshell primer mix it is necessary to add an oxygen donor and one or more fuels which tend to diminish the violence of the explosion by dilution and which by combination with the oxygen donor tend to improve the heat output and powder igniting efficiency of the mixture.

One suitable fuel is calcium silicide (Ca $Si_2$) and 55 grams of that material (dry weight) may be combined with the moist explosive ingredients in a 4 minute mixing cycle in the Hobart mixer during which the temperature will be lowered to about 92° F.

Another suitable fuel is antimony sulfide ($Sb_2S_3$) and 70 grams of this fuel (dry weight) is combined with 415 grams of barium nitrate (dry weight). These materials are premixed with each other and then mixed into the explosive mixture produced above by two successive 2 minute mixing cycles in the Hobart mixer.

The yield is about 1,145 grams of moist, plastic, shotshell priming mixture which in the moist state is insensitive to shock, friction or static electricity and which can be wet charged into primer cups in the traditional way and may be provided with the usual anvil and battery cup.

EXAMPLE IV

A shotshell priming mixture may also be produced by the following procedure:

Calcium silicide which is used as a fuel in primers does not enter into the reaction producing lead styphnate and may, if desired, be incorporated in the initial portion of the process. In this example 11 oz. (312 grams) of calcium silicide (dry weight), 7 oz. (198 cc's)

of water, 1 oz. (28 grams) of gum solution of a concentration similar to that described above in EXAMPLES I and II, 3 lbs., 7.6 oz. (1,575 grams) of styphnic acid (wet with 20% water) and 12 oz. (340 grams) of tetracene (wet with 33⅓% water) are combined in the kettle of an industrial type Hobart mixer and premixed for about 1 minute at room temperature.

A hollow is formed in the center of this moist mass of premix and in this hollow there is added 1 lb., 4.6 oz. (584 grams) dry weight of litharge and these ingredients are mixed for about 3 minutes in the Hobart mixer. As the ingredients react the temperature may rise to about 106° F.

Another hollow is formed in the center of the mass of partially reacted material and an additional quantity of 1 lb., 4.6 oz. (584 grams) (dry weight) of litharge is added in this hollow and mixing continued in the Hobart mixer for about 4 minutes. The temperature may rise to about 115° F. and the reaction should be complete. Mixing may be continued for about another 4 minutes and the temperature should fall to about 98° F.

The remaining ingredients of a shotshell priming mixture are more fuel and an oxygen donor. To complete the mixture 14 oz. (397 grams) of antimony sulfide (dry weight) and 5 lbs., 5 oz. (2,407 grams) of barium nitrate (dry weight) are separately premixed and then blended with the moist explosive ingredients in two successive 2 minute cycles in the Hobart mixer.

The yield is about 14 1/5 lbs. (6,440 grams) of moist, plastic, shotshell priming mixture conforming substantially to that produced under EXAMPLE III and usable interchangeably therewith.

With the proper proportions of ingredients and with the maintenance of the proper conditions as set forth in the examples above, it appears that the reaction between the styphnic acid and the lead compound always goes to completion with substantially no unreacted material remaining in the mass and with no by-products of the reaction except for gases which may be released or for water which remains as water of hydration in the lead styphnate crystals or as free water which is eliminated during the normal drying of the priming mixture.

The reaction with litharge appears to be represented by the following equation:

$$PbO + (NO_2)_3C_6H(OH)_2 \rightarrow C_6H(NO_2)_3O_2Pb.H_2O$$

The reaction with lead hydroxide appears to be represented by the following equation:

$$Pb_2O(OH)_2 + 2(NO_2)_3C_6H(OH)_2 \rightarrow 2C_6H(NO_2)_3O_2Pb.H_2O + 2H_2O$$

The reaction with basic lead carbonate appears to be represented by the following equation:

$$2PbCO_3.Pb(OH)_2 + 3(NO_2)_3C_6H(OH)_2 \rightarrow 3(NO_2)_3C_6H\ O_2Pb.H_2O + 2CO_2\uparrow + H_2O$$

The reaction with lead carbonate appears to be represented by the following equation:

$$PbCO_3 + (NO_2)_3 C_6H(OH)_2 \rightarrow (NO_2)_3C_6HO_2Pb.H_2O + CO_2\uparrow$$

Thus there is no necessity for the usual processes of filtering, washing, and drying which separate out and require special handling of dangerously sensitive material.

As noted above, gum arabic, tetracene, blue dye and some fuels such as calcium silicide do not enter into the reaction or interfere with the completion of the reaction and may be incorporated with the styphnic acid prior to the reaction. Indeed, to the extent that such ingredients add water to the mixture, they contribute to maintaining the moisture content which is necessary for the reaction to proceed and for safety reasons. Other ingredients, and particularly an oxygen donor such as lead nitrate or barium nitrate, should definitely not be added to the mixture until the reaction producing lead styphnate has been completed.

It may be noted that I prefer to use barium nitrate as the oxygen donor on the basis that its use tends to minimize the amount of lead discharged into the air as the result of handling or the explosion of the reactants or the final priming charge. Although mixtures using barium nitrate tend to be less percussion sensitive than mixtures using lead nitrate, the lead styphnate produced by my new process is more percussion sensitive than the prior art lead styphnate so that there is a net gain in percussion sensitivity using my new process.

It has been noted above that I prefer to add the lead compound in two steps. My earilier work on this process demonstrated that a more powerful and more percussion sensitive lead styphnate resulted when this procedure was followed. I believe that this effect is the result of a more complete reaction and that it results in the formation of somewhat different crystalline forms of lead styphnate. Thus, I prefer to add one half of the stoichiometric amount of lead oxide (or lead hydroxide, basic lead carbonate, or lead carbonate) to the styphnic acid in a first mixing cycle followed by the addition of the second half of the stoichiometric amount of lead oxide (or lead hydroxide, basic lead) carbonate, or lead carbonate) to the styphnic acid in a single mixing cycle.

In a recent study of typical rim fire priming mixtures corresponding generally to EXAMPLES I and II, identical quantities of identical materials were reacted first in the two step mixing cycle and secondly in a single step mixing cycle. When the resulting priming mixtures were charged in identical quantities and in the same manner in 22 Long Rifle rim fire cartridge cases and tested for drop test sensitivity to percussion, the product of the two step cycle had a sensitivity of $\overline{X}$ 4.14 inches and $\sigma$1.35 inches while the product of the single step mixing cycle had a sensitivity of $\overline{X}$ 5.38 inches and $\sigma$1.68 inches.

The following test results show the performance of priming mix made according to the present invention.

| 22 Cal. Rim Fire Shells | | |
|---|---|---|
| Drop test 2 oz. ball - 50 per height | | |
| | Standard (lead nitrate oxidizer) | Experimental (barium nitrate oxidizer) |
| | 5.36" | 4.72" |
| | 1.42" | 1.12" |
| 22 Cal. Standard Velocity Cartridges | | |
| Velocity | 1,087 fps | 1,076 fps |
| Pressure | 15,600 psi | 15,700 psi |
| Shotshell Shooting Test | | |
| 12 Ga. H Magnum No. 1 Buck | | |
| | Std | Experimental |
| Normal Velocity | 1,142 fps | 1,142 fps |
| Pressure | 10,900 psi | 11,000 psi |
| −20° F Velocity | 826 fps | 830 fps |
| Pressure | 7,800 psi | 8,000 psi |
| +150° F Velocity | 1,185 fps | 1,170 fps |
| Pressure | 12,400 psi | 12,300 psi |

Having now described the invention, what is new and is desired to be secured by Letters Patent is:

1. The method of making a normal lead styphnate priming composition which consists of reacting styphnic acid substantially free from sulphuric acid, the nitro derivatives of resorufin, the nitro derivatives of indophenol and the nitro derivatives of resazurin in the presence of water with an inorganic non-explosive compound of lead selected from the group of lead compounds consisting of lead oxide, basic lead carbonate, lead carbonate, and lead hydroxide to produce a workable, granular, wet mass of normal lead styphnate, and no by-products of the reaction except water or water and carbon dioxide said reaction taking place in the presence of gum arabic and a tetracene sensitizer incorporated in the reacting mass and, after the reaction has been completed, incorporated in the workable granular still wet mass an oxygen donor and a frictionator.

2. The method of claim 1, wherein the stoichiometric amount of the inorganic non-explosive lead compound is divided into at least two substantially equal parts and those equal parts are reacted in turn with the whole quantity of the styphnic acid in separate but successive mixing cycles.

3. The method of making a priming composition for ammunition which consists of mixing styphnic acid which is substantially free from sulphuric acid, the nitro derivatives of resorufin, the nitro derivatives of indophenol, and the nitro derivatives of resazurin, in the presence of water with gum arabic and tetracene, and reacting with the styphnic acid an inorganic non-explosive lead compound selected from the group lead compounds consisting of lead oxide, basic lead carbonate, lead carbonate, and lead hydroxide to produce a workable, granular, wet mass of normal lead styphnate, tetracene and gum arabic and no by-products of the reaction except water or water and carbon dioxide and then incorporating in said workable, granular still wet mass oxygen donors selected from the group of oxygen donors consisting of barium nitrate, and lead nitrate, and a ground glass frictionator.

4. The method of claim 3, wherein the stoichiometric amount of the inorganic non-explosive lead compound is divided into at least two substantially equal parts and those equal parts are reacted in turn with the whole quantity of the styphnic acid in separate but successive mixing cycles.

5. The method of claim 5 including the incorporation in said workable granular still wet mass of a fuel selected from the group of primer fuels consisting of calcium silicide and antimony sulfide.

* * * * *